(12) United States Patent
Brazeal, Jr. et al.

(10) Patent No.: US 6,212,130 B1
(45) Date of Patent: Apr. 3, 2001

(54) METHOD AND APPARATUS FOR PLURAL DOCUMENT DETECTION

(75) Inventors: Earl H. Brazeal, Jr., Coventry; James D. Callahan, Manchester; James M. Soussounis, Vernon; David H. Stone, West Hartford, all of CT (US)

(73) Assignee: Scan-Optics, Inc., Manchester, CT (US)

( * ) Notice: Subject to any disclaimer, the term of this patent is extended or adjusted under 35 U.S.C. 154(b) by 0 days.

(21) Appl. No.: 09/264,258

(22) Filed: Mar. 8, 1999

(51) Int. Cl.[7] .................................................. G01S 15/00
(52) U.S. Cl. ......................... 367/93; 271/258.01; 340/674
(58) Field of Search ............................... 367/93; 340/673, 340/674; 324/71.1; 702/171; 271/256, 258.01, 258.04

(56) References Cited

U.S. PATENT DOCUMENTS

| | | | |
|---|---|---|---|
| 4,066,969 | * | 1/1978 | Pearce et al. ..................... 271/263 X |
| 4,368,438 | * | 1/1983 | Stienstra ........................... 340/675 X |
| 5,005,192 | * | 4/1991 | Duss ...................................... 377/8 |
| 5,348,286 | * | 9/1994 | Buck .................................. 271/263 |

FOREIGN PATENT DOCUMENTS 36 20 042 A1   8/1987  (DE) .
0033552 A1   12/1981  (EP) .

\* cited by examiner

*Primary Examiner*—Thomas Mullen
(74) *Attorney, Agent, or Firm*—Alix, Yale & Ristas, LLP

(57) ABSTRACT

The presence of overlapped sheets on a paper transport is detected by employing such sheets as an acoustic interference filter. A beam of ultrasonic energy of appropriate frequency, angularly oriented to the planar transport path, will be attenuated to a much greater extent than the attenuation calculated based on the attenuation of a single sheet, as a result of destructive combining of wavefronts reflected from the facing surfaces of the overlapped sheets.

18 Claims, 3 Drawing Sheets

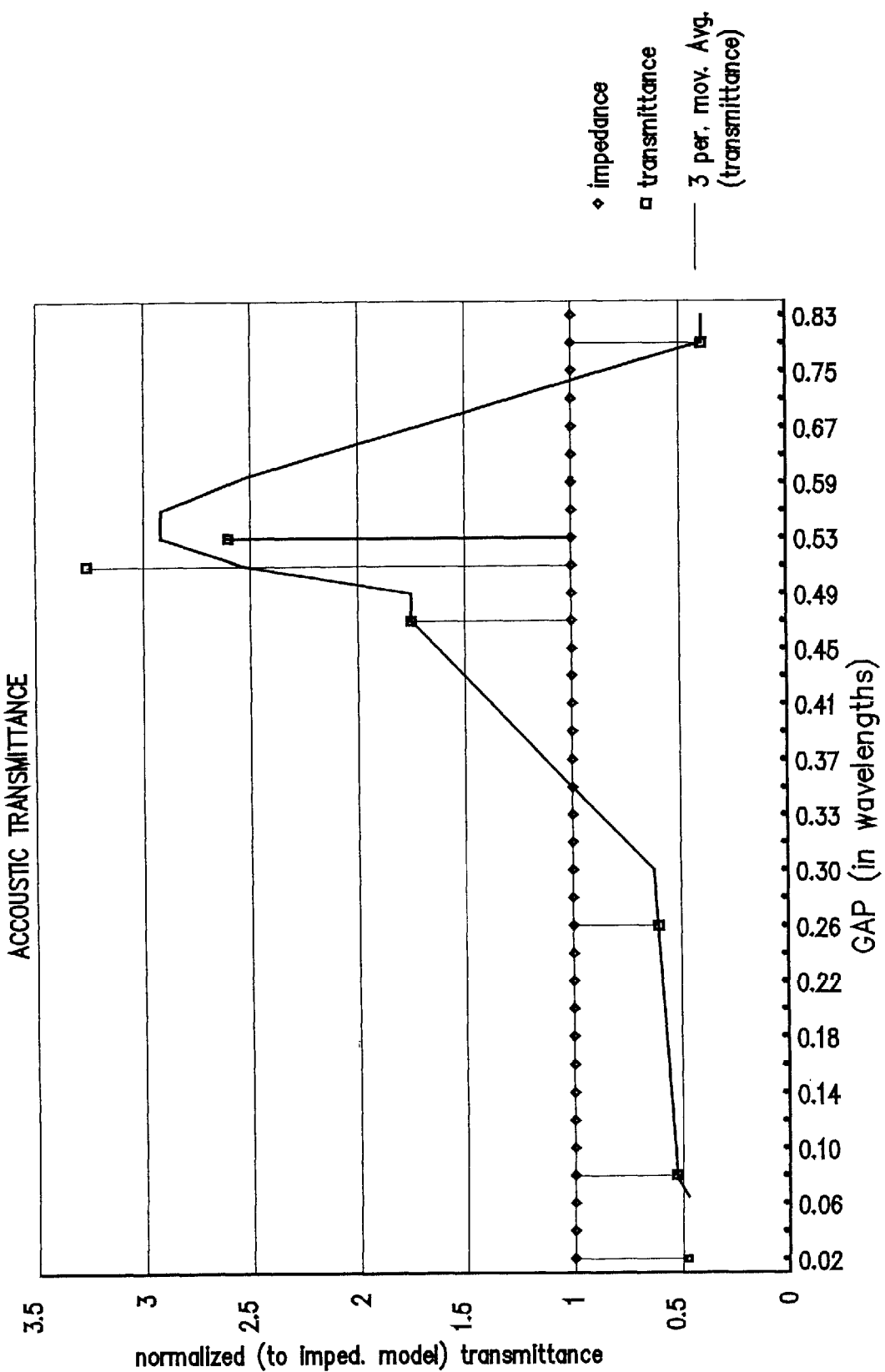

METHOD AND APPARATUS FOR PLURAL DOCUMENT DETECTION

BACKGROUND OF THE INVENTION

1. Field of the Invention

The present invention relates to the movement of documents, for purposes of capturing an image thereof, and particularly to the detection of the presence of overlapping sheets on a transport. More specifically, this invention is directed to a sensor for detecting the presence of multiple layers of sheet material, paper bearing printed indicia for example, and especially to an acoustic device for discriminating between single and plural moving thin sheets which are in surface contact. Accordingly, the general objects of the present invention are to provide novel and improved methods and apparatus of such character.

2. Description of the Related Art

In the processing of documents, for example for image capture pursuant to "machine reading", economic considerations dictate that the indicia bearing thin sheets be serially delivered to an image capture station at a high document through-put rate. The documents to be processed are customarily stacked in a magazine and individual sheets are extracted from the stack and delivered to a transport such as a vacuum conveyor. As a result of ambient operating conditions and phenomena such as electrostatic attraction and friction, multiple documents are sometimes substantially simultaneously extracted from a magazine and deposited on the transport in partial overlapping relationship or in registration with one another. The most common type of such a delivery failure is a double document feed. If the multiple fed documents are in registration, the image of the lowermost document in the viewing direction will not be captured and, accordingly, important data will not be read and processed. If the multiple fed documents are partially overlapped, the end result is that the image of neither document will be captured, a feed failure will likely result and operator intervention will be required. Obviously, the former condition, i.e., registration of multiple documents, is the more insidious problem since it is less likely of the two feed failure modes to be noticed.

Various attempts have been made to detect the presence of multiple, i.e., overlapping, documents on a paper transport. The prior approaches to solving this long standing problem have embodied optical and capacitive measurement techniques. The prior approaches, however, have been too slow and/or lacking in sensitivity, unable to operate with invariance to sheet thickness or combinations of thickness and/or unable to operate with invariance to print color or print density.

SUMMARY OF THE INVENTION

The present invention overcomes the above briefly-discussed and other deficiencies and disadvantages of the prior art and, in so doing, provides a novel and reliable acoustic technique for detection of the presence of multiple thin sheets on a moving conveyor. This invention also encompasses a novel detector for implementing the aforementioned acoustic technique.

In accordance with the present invention, the acoustic equivalent of a Fabry-Perot interferometer is implemented. In a preferred embodiment, a pair of acoustic transducers are respectively arranged as a signal transmitter and receiver located on opposite sides of the document transport path. The transducers are oriented to define a signal transmission path, having an axis, for a short wavelength acoustic signal. The axis of this acoustic signal transmission path is oriented at a small angle (about 15° to 30°) with respect to the plane of the document transport path. The receiver transducer detects low level acoustic signals, the transmitter transducer radiating such signals as energy bursts. Received signals having a magnitude in excess of a preset threshold are commensurate with the presence of not more than a single sheet of paper disposed between the transmitter and receiver transducers. Multiple sheets disposed between the transmitter and receiver transducers will function as an acoustic interference filter and cause the magnitude of the acoustic energy incident upon the receiver transducer to fall below the threshold, i.e., the signal attenuation produced by the interference filter is much greater than the attenuation produced by one sheet multiplied by the number of sheets which are present. This large drop in acoustic signal transmittance is detected and provides a reliable indication of the occurrence of a misfeed.

BRIEF DESCRIPTION OF THE DRAWINGS

The present invention may be better understood, and its numerous objects and advantages will become apparent to those skilled in the art, by reference to the accompanying drawings wherein:

FIG. 3 is a chart illustrating acoustic transmittance as a function of the magnitude of the air gap between two overlapping sheets.

DESCRIPTION OF THE DISCLOSED EMBODIMENT

In the practice of the present invention, the presence of multiple sheets of paper moving along a transport path is detected by monitoring the attenuation of a beam of acoustic energy which is transmitted across the transport path. The attenuation is, of course, minimum if there is only an air gap between an acoustic signal transmitter and receiver positioned on opposite sides of the transport path. When a single thin sheet is introduced into the air gap, there will be some attenuation, i.e., there will be a reduction in the transmittance of the acoustic signal as a function of the acoustic impedance of the sheet. The transmittance is further reduced when two overlapping thin sheets are introduced into the air gap between the transmitter and receiver transducers. In accordance with the invention, however, this further reduction in transmittance is not proportional to the corresponding change in acoustic impedance attributed solely to the second thin sheet. Thus, as will be explained below, under the controlled conditions of the invention, the attenuation of the transmitted acoustic energy when two sheets are present in the air gap is much greater than twice the attenuation which occurs with a single sheet present in the gap. Restated, under the controlled conditions of the invention, there is a radical reduction in acoustic transmittance when two thin sheets are introduced into the air gap. The difference in received acoustic signal magnitude may be detected, i.e., a signal commensurate with the acoustic energy incident on the receiver transducer may be compared with a reference signal level to provide an unambiguous and highly reliable indication of the presence of multiple sheets in the air gap.

The present invention functions, in the manner briefly and generally described above, by implementation of an acoustic analogy to a Fabry-Perot interferometer, i.e., the presence of multiple sheets in the air gap between the acoustic signal transmitter and receiver will create an interference filter. If sound waves having a wavelength, Y, are passed through two thin sheets separated by an air gap, X, the wavefronts of reflected sound energy constructively and destructively combine as a function of the distance X between the sheets. Maximum constructive interference (i.e., maximum transmittance or minimum attenuation) occurs when the acoustic path difference is an integral number of whole wavelengths, i.e., when:

$$mY \cong 2X \text{ where } m=1, 2, 3 \ldots$$

The attenuation commensurate with destructive combining of the wavefronts can be quite high (relative to the minimum attenuation value) at a distance X which is not a sub-multiple of wavelength Y.

Figure 1:
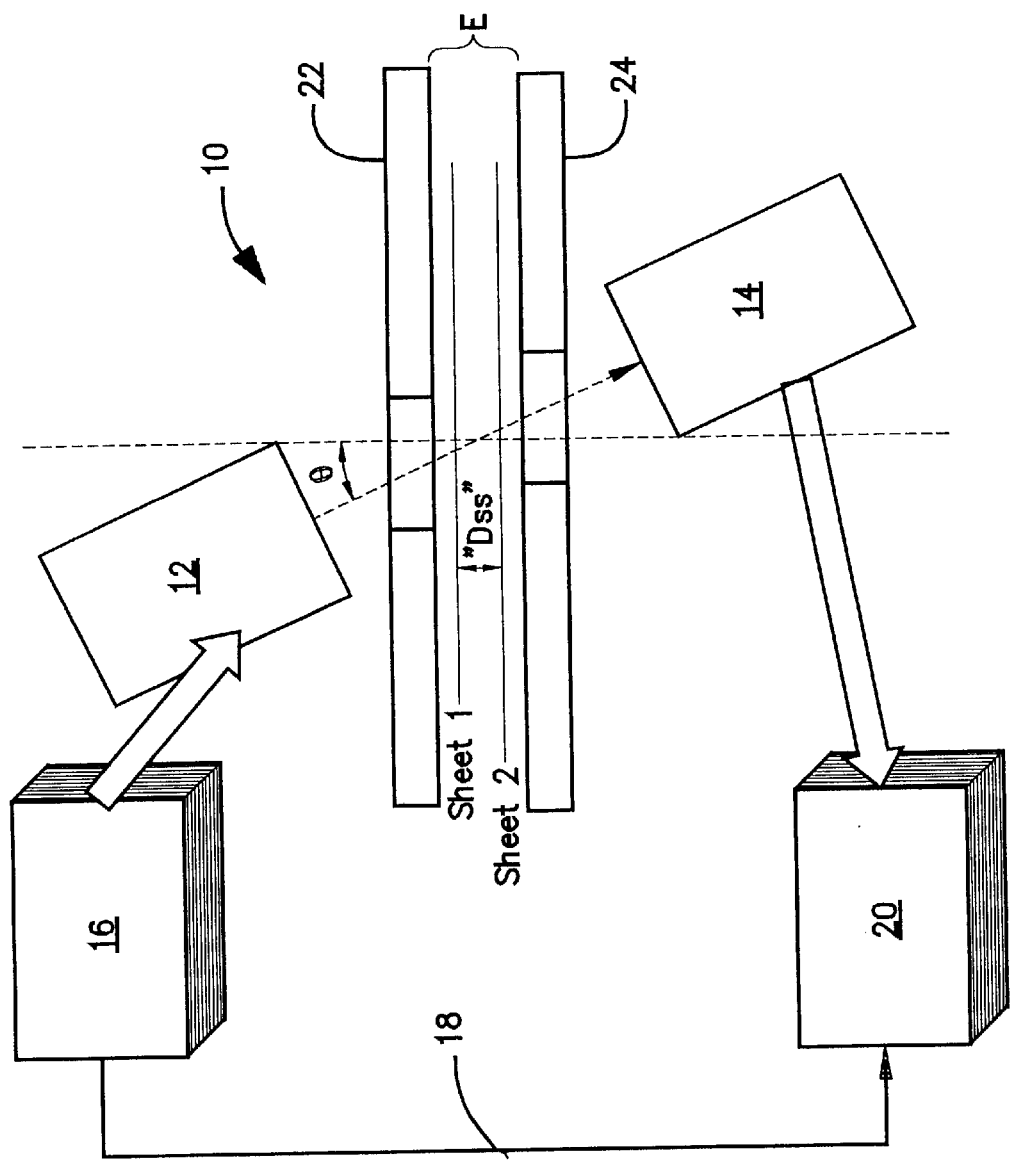
FIG. 1 is a schematic diagram depicting the mechanical arrangement of the components of one of plural channels of an apparatus in accordance with the invention.
Figure 2:
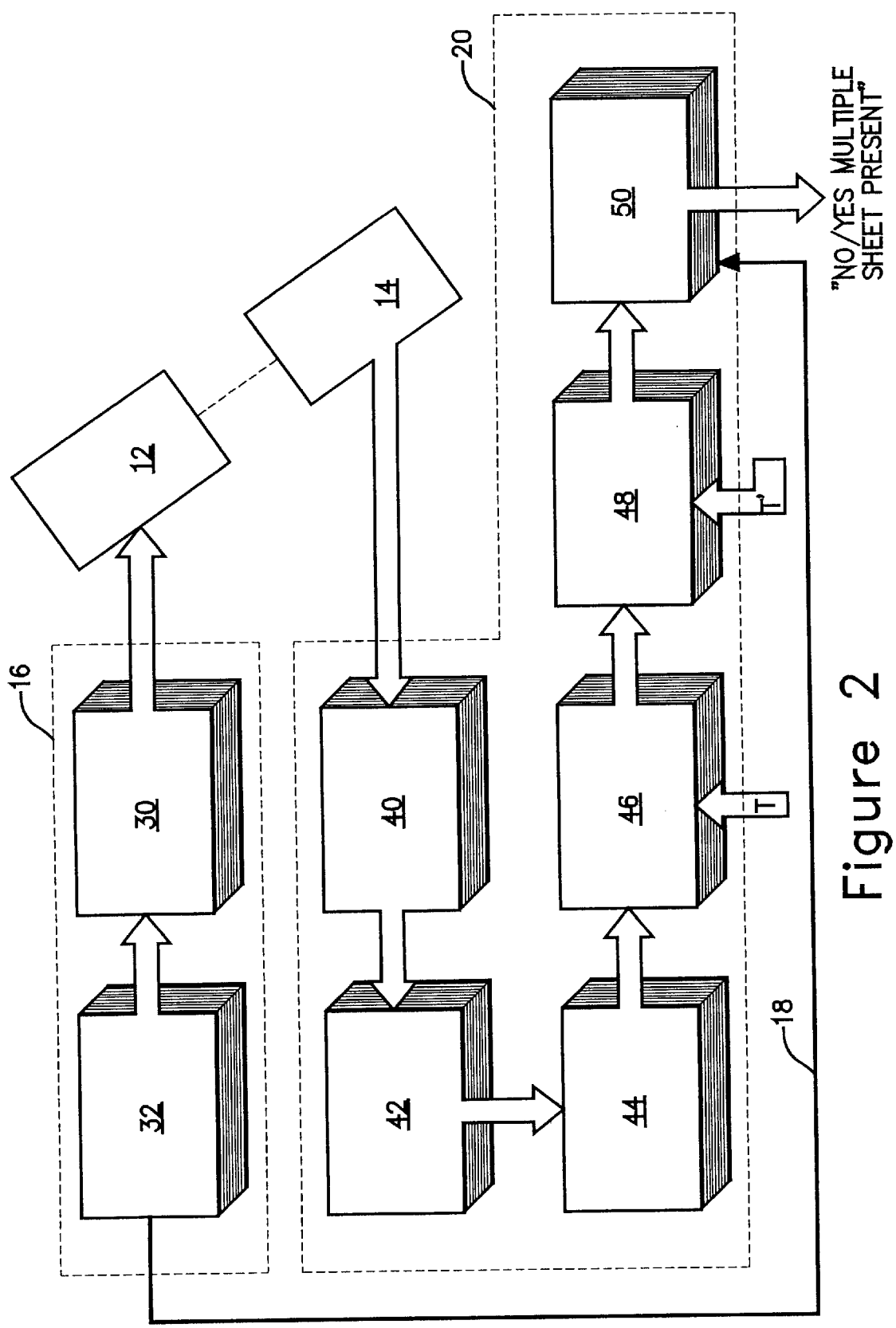
FIG. 2 is an electrical circuit block diagram of the apparatus depicted in FIG. 1.

In the reduction to practice of the present invention schematically depicted in FIGS. 1 and 2, the sheet material is paper and the acoustic wavelength Y is 1.5 mm. While the magnitude of air gap X between two overlapping thin sheets of material is a function of the sheet material, the value of X for paper has been shown to be less than 0.6 mm. Employing equation (1) above, the values of X, for minimum attenuation (maximum transmittance), are:

$$X \cong mY/2 \ (m=1, 2, 3, \ldots) \quad (2)$$

For $Y \cong 1.5$ mm, $$X \cong m \ (0.75).$$

Therefore:

| m | X(mm) | X(wavelength - Y) |
|---|-------|-------------------|
| 1 | 0.75  | 0.5Y              |
| 2 | 1.5   | 1.0Y              |
| 3 | 2.25  | 1.5Y              |

For a given wavelength, transmittance can be plotted as a function of X for a wide range of values. The resulting curve includes alternating peaks of high transmittance and valleys of low transmittance wherein the distance between two predetermined points on a single peak defines the bandwidth. In the example being discussed, Y is 1.5 mm and the physical range of X is always less than the m=1 value corresponding to minimum attenuation, i.e., in this case the sheet material is paper and, thus, $x_{max}$=0.6 mm. Accordingly, only the m=1 case need be considered.

FIG. 3 illustrates the acoustic transmittance of the example being discussed for $0 \leq X \leq 0.85Y$. As shown therein, the transmittance measured through two thin sheets does indeed vary as a function of the gap X between the sheets. In the figure, the axis labeled "normalized transmittance" represents one-half the value of single sheet transmittance normalized to a value of 1. This normalizing factor is referred to as the "impedance model". The horizontal axis is the sheet gap value X expressed in terms of wavelengths Y of the acoustic energy. The bandwidth can be taken as approximately 0.30Y (i.e., $0.45Y \leq X \leq 0.75Y$) and the transmittance for a single sheet is about 2.

At a gap X of about 0.25Y (0.38 mm), the transmittance is about ½ that of the impedance model. As the gap X approaches 0.5Y (0.75 mm), the transmittance actually increases to over several times that of the impedance model. These results are in agreement with Fabry-Perot theory.

As can be seen from FIG. 3, for many values of X an overlapping sheet condition can be easily distinguished from a single sheet condition due to the difference in the respective transmittance values. Here, the preferred value of $X_{max}$ is a function of the transmittance responses below the single sheet transmittance value of 2. The practical limit for $X_{max}$ has been empirically determined to be about 0.4Y, which is about 0.6 mm in the instant case. Naturally, other values for Y can be selected to compensate for other values of $X_{max}$ which may arise from, for example, the use of other sheet materials. Multiple sheet/single sheet conditions can also be distinguished when X and Y are selected such that the transmittance of two sheets is within the bandwidth, but well above the transmittance of a single sheet (e.g., about where X=0.5Y). However, the above-discussed example, where X is preferably about $0 \leq X \leq 0.40Y$, is preferred.

With reference now to FIGS. 1 and 2, in a typical operating environment of the present invention the documents to be processed are "stacked" with abutting sheets in surface-to-surface contact. A sheet separator, not shown, will serially "pull" either the top or the bottom sheet from the stack and deliver the thus extracted sheet to a conveyor which defines a planar transport path. It is possible that complete separation of a single sheet from the abutting sheet in the stack will not occur during extraction. In such an event, two sheets, overlapped to some degree, are delivered to the conveyor. This condition is depicted in FIG. 1 with "sheet 1" and "sheet 2". It is to be noted that the spacing between the overlapped sheets is exaggerated on FIG. 1 and the conveyor has not been depicted. The conveyor may comprise a plurality of parallel driven belts and the invention will operate in spaces between these parallel belts. In order to permit operation with documents of different width and to ensure operation independent of the lateral position of the document(s) on the transport path, an array of sensors arranged across the transport path, between each of the parallel belts for example, will be employed. FIGS. 1 and 2 depict only a single sensor channel, indicated generally at 10, comprising a transducer pair.

Sensor 10 comprises a pair of acoustic transducer devices 12, 14 which are manufactured as fixed frequency resonant circuits with low loss (high Q). As discussed above, the resonant frequency of transducers 12 and 14 is commensurate with a short acoustic wavelength. In the disclosed embodiment, transducer 12 functions as the signal transmitter while transducer 14 functions as the receiver. Transmitter transducer 12 is energized by a drive circuit 16 of conventional construction. The electrical output signals provided by drive circuit 16 cause the generation of bursts of ultrasonic energy. In reductions to practice of the invention, each burst of acoustic energy comprised between three (3) and seven (7) cycles at the resonant frequency of transducer 12. Drive circuit 16 also provides a gating control signal which is delivered, via conductor 18, to a receive/processing circuit 20.

The transmitter transducer 12 is configured to generate a beam of ultrasonic energy. The receiver transducer 14 is axially aligned with transmitter transducer 12. Acoustic energy incident on transducer 14 will be detected, i.e., will be converted into an electrical signal by the receiver transducer. Receiver transducer 14, accordingly, will detect low level "burst" signals corresponding to the output of transmitter transducer 12 and produce electrical signals commensurate therewith. The electrical output signals of transducer 14, i.e., the envelope corresponding to the received bursts of acoustic energy, are delivered to the receiving circuit 20. In the manner to be described below in the discussion of FIG. 2, the envelope of each received "burst" will be processed by the receiver circuit 20. Received signals that exceed a preset threshold will be recognized as "single sheets". Received signals that fall below the threshold will be indicative of "multiple sheets", i.e., the presence of an acoustic interference filter in the signal path between transducers 12 and 14.

Operation of the invention is predicated upon the proper positioning and orientation of transducers 12 and 14 on opposite sides of the paper path. In the disclosed embodiment, a pair of apertured guide plates 22 and 24 are respectively positioned on the same side of the paper path as transmitter transducer 12 and receiver transducer 14. As discussed above, the axis of the beam of ultrasonic energy produced by transducer 12 must be inclined at an angle θ with respect to a line normal to plates 22 and 24, the beam axis thus also being angularly inclined relative to the surfaces of the thin sheets moving along the transport path. The gap E between the facing surfaces of plates 22 and 24 is chosen to eliminate the constructive combination condition depicted in FIG. 3. Accordingly, gap E is preferably less than about one-half the wavelength Y of the radiated acoustic energy. The apertures in plates 22 and 24 through which the acoustic energy passes have a diameter which is greater than wavelength Y. In one reduction to practice, the apertures in plates 22 and 24 were circular and had a diameter which was 4Y (6.0 mm).

In operation, an acoustic wavefront emanating from transducer 12 will propagate through the aperture in guide plate 22, cross gap E, pass through the aperture in guide plate 24 and be incident upon transducer 14. Transducer 14 will produce electrical output signals having a magnitude and shape which corresponds to the incident acoustic energy. Referring to FIG. 2, transducer 12 is excited to generate bursts of acoustic energy by a driver/oscillator 30 operating under control of a timing signal generator 32. The receive/processing circuit 20 comprises a band-pass gain stage 40, 42, consisting of a two stage amplifier. The amplification is followed by full-wave detection by a detector 44. Detector 44, in one reduction to practice, comprised an operational amplifier and diode configuration. The output of detector 44 is a full-wave rectified burst signal which is delivered as the INPUT signal to an envelope "thresholder" 46, i.e., an adjustable comparator circuit which generates an output signal (OUTPUT–INPUT) if, and only if, the INPUT>T, where T is the variable threshold value. Circuit 46 may, for example, be a low pass filter operational amplifier with an offset adjustment and a feedback diode. The thresholder circuit 46 is configured such that its OUTPUT=0 when the INPUT from detector 44 is less than or equal to the threshold (offset) T. The output of thresholder circuit 46 will, when the INPUT>T threshold condition is satisfied, be a signal commensurate with the peak envelope magnitude of each burst of ultrasonic energy incident on transducer 14 offset by the setting of the threshold T. The value of threshold signal T is commensurate with the absence of a sheet of paper in gap E or the presence of one sheet in gap E. Thus, thresholder circuit 46 will provide a positive output signal level (INPUT>T) when the acoustic energy incident on receiver transducer 14 is, when compared to the signal radiated by transducer 12, minimally attenuated. However, if the input signal to thresholder circuit 46 is indicative of substantial attenuation, a low amplitude or zero value output signal is generated. The output signals from circuit 46 are delivered as a first input to a comparator circuit 48. Circuit 48 will receive, as a further input, a second threshold signal T' commensurate with a minimum level of background noise, i.e., "clutter". Comparator circuit 48 comprises an operational amplifier with positive feedback and a fixed input offset, i.e., signal T'. The output of circuit 48 is delivered to an output logic circuit 50. Logic circuit 50 provides time gated output signals, which may be used for control purposes, commensurate with the presence or absence of multiple sheets in gap E.

Considering now the conditions which might be encountered during operation of the invention, with no document present in gap E, the acoustic wavefront will arrive at transducer 14 with minimal attenuation. Thus, the output of envelope thresholder 46 will be a positive signal commensurate with the maximum amplitude envelope. The comparison and gating of this signal performed by circuits 48 and 50 will result in logic circuit 50 providing a "NO MULTIPLE SHEET PRESENT" output signal.

When a single sheet is present in gap E, operation will be substantially the same as described in the immediately preceding paragraph. There will, of course, be some attenuation of the acoustic energy through the thin media. The gain of the receive circuit 20, however, is such that the input to thresholder 46 will exceed THRESHOLD T and, accordingly, the "NO MULTIPLE SHEET PRESENT" output will be provided by logic circuit 50.

Under the condition depicted in FIG. 1, the multiple overlapping thin sheets in gap E form an interference filter, i.e., the sonic equivalent of a Fabry-Perot interferometer. With a surface-to-surface distance between these sheets, Dss or $X \cong \frac{1}{2} Ym$ (m=1, 2, 3, ...), minimal attenuation of the burst of acoustic energy occurs. However, high attenuation occurs at other distance values due to destructive interference of reflected waves. The angular orientation of the ultrasonic energy beam axis eliminates the guide plates and transducer surfaces as possible reflectors, thus reducing the possibility of a false minimal attenuation situation being encountered. Further, the distance between sheet 1 and sheet 2 is constrained to a gap of less than (½)Y. Thus, the probability of encountering the dimension Dss or X which will result in a minimal attenuation condition is small. The likelihood of maximum attenuation is much greater than the minimal attenuation condition and, accordingly, the receiver circuit 20 will generate the "YES MULTIPLE SHEET PRESENT" alarm output with very high probability when there are in fact multiple overlapping sheets present in gap E.

While a preferred embodiment has been shown and described, various modifications and substitutions may be made thereto without departing from the spirit and scope of the invention. Accordingly, it is to be understood that the present invention has been described by way of illustration and not limitation.

What is claimed is:

1. A method for the detection of overlapped sheets, the sheets being conveyed along a transport path and being supported in a plane during movement, said method comprising the steps of:

positioning an ultrasound beam generator on a first side of the transport path, the beam generator producing a beam of ultrasound energy having a frequency and an axis and being oriented such that the axis of the beam of ultrasound energy produced thereby intersects the plane in which the sheets are supported at an acute angle;

locating an ultrasound receiver on the second side of the transport path and in axial alignment with the beam generator, an air gap through which the sheets are transported thus being present between the beam generator and beam receiver, the ultrasound receiver providing electrical signals commensurate with ultrasonic energy incident thereon;

selecting the frequency of the ultrasound energy such that multiple sheets present in the air gap will function as an interference filter whereby the wavefronts of the transmitted ultrasound energy will destructively combine and the degree of attenuation will be substantially greater than that caused by a single sheet;

energizing the ultrasound beam generator to cause the production of bursts of energy at the selected frequency;

determining from the signals provided by the receiver whether the degree of attenuation of ultrasound energy which traverses the air gap between the beam generator and ultrasound receiver is commensurate with the presence of closely spaced plural sheets in the air gap; and providing an alarm when the degree of attenuation of the ultrasound energy is indicative of plural sheets being present in the path of the beam of ultrasound energy.

2. The method of claim 1 wherein the sheets being transported are thin sheets of paper, wherein the spacing between facing surfaces of a pair of overlapping sheets is less than 1 mm and the frequency of the ultrasound energy is commensurate with a wavelength of greater than 1 mm.

3. The method of claim 1 wherein the step of determining comprises:

comparing the signals provided by the receiver with a first reference level commensurate with a degree of attenuation corresponding to not more than one sheet in the air gap; and employing the results of the comparison to produce a control signal having first and second levels, said control signal levels being respectively indicative of multiple sheets and not more than one sheet in the air gap.

4. The method of claim 3 wherein the sheets being transported are thin sheets of paper, wherein the spacing between facing surfaces of a pair of overlapping sheets is less than 1 mm and the frequency of the ultrasound energy is commensurate with a wavelength of greater than 1 mm.

5. The method of claim 3 wherein the spacing between facing surfaces of overlapping sheets is less than or equal to about 0.40 times the wavelength of the ultrasound energy.

6. The method of claim 1 wherein the sheets being transported are thin sheets of paper, and wherein the wavelength of the ultrasound energy is selected to prevent constructive reflecting wavefronts based on the spacing between facing surfaces of overlapping sheets of the transported paper.

7. The method of claim 1 wherein the spacing between facing surfaces of a pair of overlapping sheets is less than or equal to about 0.6 mm, wherein the wavelength of the ultrasound energy is about 1.5 mm and wherein the sheets are paper.

8. Apparatus for detecting the presence of overlapped sheets on a transport, the transport defining a substantially planar path along which the sheets are linearly conveyed, said detecting apparatus comprising:

an ultrasound beam generator, said beam generator radiating bursts of ultrasonic energy at a preselected frequency, the radiated energy comprising wavefronts which move generally in the direction of the beam axis, the beam generator being supported on a first side of the transport path such that the beam axis intersects the plane of the transport path at an acute angle, said preselected frequency being commensurate with a wavelength which is greater than the largest spacing between facing surfaces of a pair of overlapping sheets being conveyed by the transport and said frequency and angle being selected such that overlapped sheets in said air gap will function as an interference filter and the wavefronts of the radiated ultrasound energy will destructively combine;

a receiver transducer, said receiver transducer generating electrical output signals commensurate with ultrasonic energy incident thereon, said receiver transducer being supported on the second side of the transport path in alignment with said beam axis, an air gap through which the sheets being transported will pass being defined between said beam generator and receiver transducer;

an attenuation detector responsive to output signals provided by said receiver transducer and at least a first reference signal, said first reference signal being commensurate with an output signal produced by said receiver in the absence of multiple sheets of paper in said air gap, said attenuation detector providing a control signal indicative of results of a comparison of said receiver transducer output signal and said first reference signal; and an alarm signal generator responsive to the output of said attenuation detector, said alarm signal generator providing an output signal indicative of the presence of multiple overlapped sheets of paper in said air gap.

9. The apparatus of claim 8 wherein said attenuation detector comprises:

an envelope detector, said detector producing a voltage level commensurate with output signals generated by said receiver transducer; and a first comparator for comparing the voltage level produced by said envelope detector with said first reference signal.

10. The apparatus of claim 9 wherein said ultrasound beam generator includes an ultrasound transducer comprising a fixed frequency resonant circuit and a drive circuit for said beam generator transducer, said drive circuit including a timing signal generator, and wherein said alarm signal generator comprises a comparator and a logic circuit that is responsive to output signals provided by said comparator and to timing signals provided by said timing signal generator.

11. The apparatus of claim 8 further comprising:

a pair of spatially displaced guide plates, said guide plates being disposed on opposite sides of the planar transport path, the spacing between said guide plates being commensurate with the wavelength of said preselected ultrasound frequency, said guide plates each being provided with an aperture which is at least substantially coaxial with said beam of ultrasonic energy, the ultrasonic energy generated by said beam generator passing through the aperture in a first of said guide plates, traversing said air gap, passing through the aperture in the other of said guide plates and being incident upon said receiver transducer.

12. The apparatus of claim 11 wherein said attenuation detector comprises:

an envelope detector, said detector producing a voltage level commensurate with output signals generated by said receiver transducer; and a first comparator for comparing the voltage level produced by said envelope detector with said first reference signal.

13. The apparatus of claim 12 wherein said ultrasound beam generator includes an ultrasound transducer comprising a fixed frequency resonant circuit and a drive circuit for said beam generator transducer, said drive circuit including a timing signal generator, and wherein said alarm signal generator comprises a comparator and a logic circuit that is responsive to output signals provided by said comparator and to timing signals provided by said timing signal generator.

14. The apparatus of claim 8 wherein the largest spacing between facing surfaces of a pair of overlapping sheets is about 0.4 times the wavelength of said preselected frequency such that overlapping sheets in said air gap will function as an interference filter and the wavefronts of the radiated ultrasound energy will destructively combine.

15. A method for the detection of overlapped sheets, the sheets being conveyed along a transport path and being supported in a plane during movement, said method comprising the steps of:

positioning an ultrasound beam generator on a first side of the transport path, the beam generator being oriented such that the axis of the beam of ultrasound energy produced thereby will intersect the plane in which the sheets are supported at an acute angle;

locating an ultrasound receiver on the second side of the transport path and in axial alignment with the beam generator, an air gap through which the sheets are transported thus being present between the beam generator and beam receiver, the ultrasound receiver providing electrical signals commensurate with ultrasonic energy incident thereon;

energizing the ultrasound beam generator to cause the production of bursts of energy at a preselected frequency;

determining from the signals provided by the receiver whether the degree of attenuation of ultrasound energy which traverses the air gap between the beam generator and ultrasound receiver is commensurate with the presence of closely spaced plural sheets in the air gap; and providing an alarm when the degree of attenuation of the ultrasound energy is indicative of plural sheets being present in the path of the beam of ultrasound energy.

16. The method of claim 15 wherein the step of energizing the beam generator comprises selecting the preselected frequency such that multiple sheets present in the air gap will function as an interference filter whereby the wavefronts of the transmitted ultrasound energy will destructively combine and the degree of attenuation will be much greater than that caused by a single sheet.

17. Apparatus for detecting the presence of overlapped sheets on a transport, the transport defining a substantially planar path along which the sheets are linearly conveyed, said detecting apparatus comprising:

an ultrasound beam generator, said beam generator radiating bursts of ultrasonic energy at a preselected frequency, the radiated energy comprising wavefronts which move generally in the direction of the beam axis, the beam generator being supported on a first side of the transport path such that the beam axis intersects the plane of the transport path at an acute angle;

a receiver transducer, said receiver transducer generating electrical output signals commensurate with ultrasonic energy incident thereon, said receiver transducer being supported on the second side of the transport path in alignment with said beam axis, an air gap through which the sheets being transported will pass being defined between said beam generator and receiver transducer;

an attenuation detector responsive to output signals provided by said receiver transducer and at least a first reference signal, said first reference signal being commensurate with an output signal produced by said receiver in the absence of multiple sheets of paper in said air gap, said attenuation detector providing a control signal indicative of results of a comparison of said receiver transducer output signal and said first reference signal; and an alarm signal generator responsive to the output of said attenuation detector, said alarm signal generator providing an output signal indicative of the presence of multiple overlapped sheets of paper in said air gap.

18. The apparatus of claim 17 wherein the spacing between facing surfaces of a pair of overlapping sheets and the wavelength of said preselected frequency have been preselected such that overlapping sheets in said air gap will function as an interference filter and the wavefronts of the radiated ultrasound energy will destructively combine.

* * * * *